United States Patent [19]

Giolito et al.

[11] 3,931,364

[45] Jan. 6, 1976

[54] COLOR IMPROVEMENT OF PHOSPHATE ESTERS

[75] Inventors: Silvio L. Giolito, Whitestone, N.Y.; Stanley B. Mirviss, Stamford, Conn.

[73] Assignee: Stauffer Chemical Company, Westport, Conn.

[22] Filed: Dec. 23, 1974

[21] Appl. No.: 535,886

[52] U.S. Cl. .................... 260/975; 260/989
[51] Int. Cl.² .............................. C07F 9/12
[58] Field of Search ..................... 260/989, 975

[56] References Cited
UNITED STATES PATENTS 3,356,775 12/1967 Mitchell .................... 260/989 X
3,681,482 8/1972 Patel et al. .................. 260/989

*Primary Examiner*—Richard L. Raymond
*Attorney, Agent, or Firm*—Charles B. Rodman

[57] ABSTRACT

A method for decolorizing and stabilizing alkylphenyl esters of phosphoric acid which comprises contacting the esters with an effective amount of a phosphite ester for a sufficient length of time to decolorize and stabilize the esters against subsequent color formation.

11 Claims, No Drawings

COLOR IMPROVEMENT OF PHOSPHATE ESTERS

BACKGROUND OF THE INVENTION

This invention relates to the decolorization and stabilization of alkylphenyl esters of phosphoric acid. The production of low color and color stable phosphate esters from alkylphenol precursors has been a long recognized problem. In the conventional production of phosphate esters from alkylphenols, undesirable color formation frequently occurs. Color can decrease the phosphate ester's value as a commercial product.

Alkylphenyl esters of phosphoric acid find extensive use as plasticizers for nitrocellulose and polyvinyl chloride (PVC) compositions. In addition, they also serve as additives for gasoline, functional fluids, oils, and are useful as flame retardants in plastics, and the like.

The preparation of alkylphenyl esters of phosphoric acid is generally accomplished by the addition of phosphorus oxychloride, ($POCl_3$) to selected phenols, such as cresols, xylenols, and the like, and gradually heating the resulting reaction mixture to about 180°C. The reaction is accelerated by the presence of a Friedel-Crafts catalyst such as aluminum chloride, ($AlCl_3$). In conventional processing, the reaction product is vacuum distilled to remove unreacted phenols as an initial fraction, and the alkylphenyl phosphate ester as a product fraction, leaving high boiling point materials and the catalyst in the residue. The distilled product fraction is then washed thoroughly with sodium hydroxide solution to remove the free phenol and acidic materials, followed by water washing. The product fraction is then generally treated with activated carbon to remove color causing impurities.

This process, which works very well with esters produced from conventional by-product alkylphenols, produces unsatisfactory material when applied to mixed alkylphenols produced by the alkylation of phenol with olefins. It is found that the products discolor upon exposure to air, exposure to heat, or storage in the dark. The discoloration has been attributed to the presence of di(o-alkyl) phenols in the alkylated phenol. Steric hindrance caused by the double ortho substitution in 2,6-dialkylphenols and in 2,4,6-trialkylphenols renders the phenols unresponsive to washing with sodium hydroxide solution, so that they are not removed by the caustic wash.

These so called "hindered phenols," can oxidize in the presence of air to form highly colored quinones, which are the source of undesirable discoloration in the product. These quinones can bleach somewhat in the light, however, color will reappear upon storage in the dark. The color can intensify when the ester is mixed or milled with polyvinyl chloride (PVC) under the influence of air and heat.

Thus, for example, in the case of 2,6-diisopropylphenol, the corresponding diphenoquinone or benzoquinone is highly colored. Esters made from mixtures of alkylated phenols which contain di-orthoalkylphenols such as 2,6-diisopropylphenol can be too highly colored for many uses, particularly for use as plasticizers. High color phosphate esters have limited utility for plasticizer use and are less marketable.

Color formation in phosphate esters is discussed in U.S. Pat. No. 3,681,482, which correlates the degree of color formation in phosphate esters to the degree of alkyl substitution of the aryl ring. Accordingly, tris(methylphenyl) phosphate will produce less color than tris(dimethylphenyl) phosphate. This may be explained by the fact that the tris(methylphenyl) phosphate has only one methyl group substituted on the aryl ring, whereas tris(dimethylphenyl) phosphate has two methyl groups substituted on the aryl ring and, therefore, has more color.

A number of proposals have been made for methods to overcome the problem of undesirable color formation. For example, U.S. Pat. No. 1,958,210 discloses the use of activated carbon to decolorize and remove oxidizable impurities from phosphate esters. In certain instances, for example, in the decolorization of isopropylphenyl diphenyl phosphate ester, the use of activated carbon may increase color formation.

U.S. Pat. No. 2,113,951 discloses a method wherein an alkylphenol such as cresylic acid is distilled in the presence of a mineral acid such as sulfuric, hydrochloric or phosphoric acid, to purify it. The purified cresylic acid is then employed in the manufacture of tricresyl phosphate esters which are supposed to be more stable to the action of heat and light than the corresponding ester made from alkylphenols distilled in the absence of an inorganic acid. The disadvantage of this process is that the phenolic residues oxidize to colored quinones, and must be thoroughly distilled in order to remove them and avoid further color formation.

Another method for reducing color is proposed in U.S. Pat. No. 3,681,492 wherein sodium borohydride is used to permanently bleach and color stabilizie tris(alkylphenyl) phosphate esters containing 2,6-diisopropylphenol and the corresponding diphenoquinone. The sodium borohydride reduces the diphenoquinone to the colorless 2,6-diisopropylphenol which, however, remains in the product and is a potential source of discoloration if the product is exposed to oxidizing conditions. Sodium borohydride treatment is also expensive in cost of materials and time, as several hours to overnight treating times are necessary.

Thus, it can be seen that the methods proposed in the prior art, are not commercially effective for removing color from alkylphenol esters of phosphoric acid, or do not improve the PVC mill stability when these esters are used as PVC plasticizers.

SUMMARY OF INVENTION

In accordance with the present invention, a method for removing color from alkylphenol esters of phosphoric acid which also improves the mill stability of these esters when they are used as plasticizers for PVC has now been discovered.

The method comprises contacting the alkylphenyl phosphate esters with an effective amount of a phosphite ester for a time sufficient to reduce the color to the desired level. The phosphate ester is decolorized and stabilized against subsequent color formation. This treatment produces a low color, stable phosphate ester and may be conducted during the sodium hydroxide wash of the phosphate ester product. The phosphite esters are generally employed in a dilute caustic solution.

DETAILED DESCRIPTION OF THE INVENTION AND THE PREFERRED EMBODIMENTS

Permanent removal of color from colored phosphate esters according to the method of this invention is achieved by contacting the phosphate ester with an effective amount of a phosphite ester with a dilute caustic solution for a time sufficient to decolorize the phosphate ester to the desired level, and stabilize it against subsequent color formation.

This invention is applicable to all phosphate esters which are made from alkylated phenol mixtures which contain hindered phenols, e.g., phenols containing alkyl groups on both positions ortho to the hydroxyl group. The esters may contain 0.5 to 3 alkylaryl groups and 0 to 2.5 phenyl groups. Preferably, the triaryl phosphate esters treated by the process of this invention are a mixture of esters containing 1 to 2 alkaryl groups. The esters correspond to the general formula:

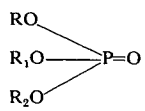

where R is alkylaryl and $R_1$ and $R_2$ may be alkyl, alkaryl, aralkyl or aryl, and wherein the alkyl groups can contain from 1 to 20 carbon atoms, more preferably from 1 to 12 carbon atoms. Some triphenylphosphate may also be present.

The alkylated phenols which contain hindered phenols are usually made by alkylating phenol with $C_2$-$C_{12}$ unsaturated hydrocarbons such as ethylene, propylene, isobutylene and its isomers, amylene and its isomers, tripropylene, tetrapropylene, decene, dodecene, diisobutylene and the like.

Typical examples of alkyl radicals are as follows: methyl, ethyl, normal propyl, isopropyl, normal butyl, isobutyl, secondary butyl, tertiary butyl, normal amyl, isoamyl, 2-methylbutyl, 2,2-dimethyl propyl, 1-methyl butyl, diethylmethyl, 1,2-dimethyl propyl, tertiary amyl, normal hexyl, 1-methylamyl, 1-ethyl butyl, 1,2,2-trimethyl propyl, 3,3-dimethyl butyl, 1,1,2-trimethyl propyl, 2-methyl amyl, 1,1-dimethyl butyl, 1-ethyl 2-methyl propyl, 1,3-dimethyl butyl, isohexyl, 3-methylamyl, 1,2-dimethyl butyl, 1-methyl 1-ethyl propyl, 2-ethyl, normal heptyl, 1,1,2,3-tetramethyl propyl, 1,2-dimethyl 1-ethyl propyl, 1,1,2-trimethyl butyl, 1-isopropyl 2-methyl propyl, 1-methyl 2-ethyl butyl, 1,1-diethyl propyl, 2-methyl hexyl, 1,1-dimethyl amyl, 1-isopropyl butyl, 1-ethyl 3-methyl butyl, 1,4-dimethyl amyl, isoheptyl, 1-methyl 1-ethyl butyl, 1-ethyl 2-methyl butyl, 1-methyl hexyl, 1-propyl butyl, normal octyl, 1-methyl heptyl, 1,1-diethyl 2-methyl propyl, 1,1,3,3-tetramethyl butyl, 1,1-diethyl butyl, 1,1-dimethyl hexyl, 1-methyl 1-ethyl amyl, 1-methyl 1-propyl butyl, 2-ethyl hexyl, 6-methyl heptyl normal nonyl, 1-methyl octyl, 1-ethyl heptyl, 1,1-dimethyl heptyl, 1-ethyl 1-propyl butyl, 1,1-diethyl 3-methyl butyl, diisobutyl methyl, 3,5,5-trimethyl hexyl, 3,5-dimethyl heptyl, normal decyl, 1-propyl heptyl, 1,1-diethyl hexyl, 1,1-dipropyl butyl, 2-isopropyl 5-methyl hexyl and $C_{11}$-$C_{20}$ alkyl groups.

Also included are aralkyl groups, e.g., benzyl, alpha- or beta-phenylethyl, alpha,alpha dimethylbenzyl and the like. Also included are cyclohexyl, cycloheptyl, cyclododecyl and the like.

Typical examples of aryl and alkaryl radicals are phenyl, cresyl, xylyl, alkoxylated phenyl, isopropylphenyl, butylphenyl, alpha alkylbenzylphenyl and alpha,alpha-dialkylbenzylphenyl, e.g., alpha-methylbenzylphenyl, alpha,alpha-dimethylbenzylphenyl, tert-nonylphenyl, amylphenyl, tert-butylphenyl, isooctylphenyl, dodecylphenyl, tertiary octylphenyl and the like.

The invention is hereinafter exemplified by first showing the preparation of an ester via the alkylation of phenol with an olefin, followed by addition of $POCl_3$. These alkylated phenols produce esters which are similar to those produced with conventional by-product coal tar cresylic acids or methylphenols.

The esters are generally made by reacting an alkylphenol with $POCl_3$ in the presence of a Friedel-Crafts catalyst at an elevated temperature, typically about 180°C., until the reaction is complete, as noted by the cessation of HCl evolution. The reaction mixture is then heated to distill excess phenols overhead. The temperature and/or vacuum is then increased and the phosphate ester product is distilled leaving the catalyst and a small amount of high boiling distillation residue.

Conventionally, the ester product is washed with aqueous alkali to remove free phenols which are generally present in the range of about a few tenths of a percent. The washed product is separated from the water and heated, generally under vacuum and then treated with activated carbon and a filter aid, such as diatomaceous earth, and filtered. However, product discoloration caused by hindered phenols in the presence of air and heat can occur, especially during the caustic wash and/or during the drying step, rendering the product unsuitable for use in applications where lack of color is important.

In accordance with this invention, the phosphate ester is treated for color removal and color stabilization by contacting the alkylphenyl phosphate ester with an effective amount of a phosphite ester for a sufficient length of time until the color is adequately reduced. The contacting treatment is preferably conducted during the sodium hydroxide wash of the phosphate ester product.

The phosphite esters used in this invention correspond to the general formula

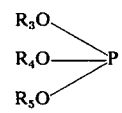

wherein $R_3$, $R_4$, and $R_5$, are radicals, each independently selected from the group consisting of alkyl, cycloalkyl, aryl, alkaryl or aralkyl, wherein the alkyl groups contain from 1 to about 20 carbon atoms, more preferably from 1 to 12 carbon atoms. Furthermore, at least one radical from the group $R_3$, $R_4$, or $R_5$ is aryl or alkaryl. Typical examples of the above radicals are as have been hereinbefore exemplified.

The triaryl phosphite esters are preferred. Trialkyl phosphites lend to odorous products and/or less effective treatment. Especially preferred are the tris(alkylaryl) phosphite esters.

Treatment times will vary, generally from about 5 minutes to about 24 hours, depending upon the amount of phosphate ester treated, the amount and concentration of phosphite ester in solution, the temperature, agitation, and the like. Preferably, the phosphate esters are washed for about 1 hour to about 5 hours at a temperature of about 20°C. to about 100°. More preferably, the washing treatment is carried out at temperatures of about 45°C. to about 70°C.

The phosphite esters are generally employed in a dilute caustic solution. The amount of phosphite ester can vary from about 0.1% to about 10% by weight of the phosphate ester treated. Larger amounts of the phosphite ester can be employed, but no advantage is accrued thereby. It is preferred to use an amount ranging from about 0.5% to about 5% by weight of the phosphate ester treated. However, it is particularly preferred to employ phosphite ester in an amount ranging from about 1% to about 3% by weight of the phosphate ester treated.

The particular amount of phosphite ester employed in any given instance will to some extent be influenced by a number of factors, which include the amount of color present, the amount of color improvement desired, the particular phosphate ester treated, treatment time and the like.

The amount of caustic solution used is about 5–200 volume percent of the phosphate ester treated, and preferably about 25–150 volume percent.

The caustic solution used may contain from about 0.1% to about 5% sodium hydroxide, potassium hydroxide and the like, preferably about 0.5% to about 3%. The washing is carried out at temperatures ranging from about 10°–85°C., preferably about 20°–70°C., for about 10–200 minutes, preferably about 20–120 minutes. The caustic-phosphite ester wash is followed by water washing until subsequent water washes are neutral.

The phosphate ester is preferably distilled before washing.

The method of this invention is generally conducted under atmospheric pressure. However, higher or lower pressures may be used. It may also be conducted under an inert atmosphere, such as nitrogen which serves to repress re-oxidation.

The method of this invention may be carried out batchwise or in a continuous manner. One particular advantage of the instant invention is that after treatment of the phosphate ester with the phosphite ester solution, no additional steps or special treatment other than an optional washing step, phase separation and drying are necessary. Residual phosphite esters do not appear to have an adverse effect on the commercial properties of the phosphate esters.

In general, the process consists of:
1. Phosphorylation
2. Distillation of the product;
3. Sampling of an initial fraction which contains the bulk portion of unreacted free phenols, which can be discarded or recycled back to the phosphorylation step;
4. Washing the distilled phosphate ester with a caustic solution containing the triaryl phosphite (which may not be fully dissolved). This is an aqueous solution;
5. Water washing until the final water wash is essentially neutral;
6. Washing with dilute phosphoric acid (optional);
7. Washing with water (optional);
8. Drying the phosphate ester.

The following examples are illustrative of the methods disclosed above, and are provided without any intention that the invention be limited thereto. In the examples and throughout the specification, all parts and percentages are by weight, unless otherwise noted.

EXAMPLE 1

Preparation of Isopropylphenyl Diphenyl Phosphate Ester 1.86 moles of phenol, 1.50 moles of an isopropylphenol mixture containing mono- and diisopropyl phenols, and 1.12 moles of phosphorus oxychloride were placed in a 1 liter reactor and stirred at a moderate rate at room temperature. Nitrogen gas was bubbled slowly through the liquid and anhydrous magnesium chloride catalyst was added to the stirred contents. The charge was then heated, while slowly being stirred, from a temperature of 38° to 180°C. over a period of 4 hours. The temperature was maintained at 180°C. for approximately 5 hours or until the evolution of hydrogen chloride ceased.

The crude isopropylphenyl diphenyl phosphate product weighing 423 grams was then transferred to a ½ liter distillation flask and vacuum distilled through a 6 × 1 inches column packed with ¼ inch glass spheres. The distilled isopropylphenyl diphenyl phosphate ester product weighing 366 grams was then introduced into a 2 liter reactor and washed for 1 hour at 65°C. with 300 milliliters of a 1% sodium hydroxide solution. The caustic wash was repeated two additional times with fresh caustic solution.

The isopropylphenyl diphenyl phosphate ester was then separated from the caustic solution and washed twice with 300 milliliters of water at 65°C. for 1 hour. The water phase after the second wash was neutral to pH paper. The washed ester was separated from the final wash water and dried at 100°C. under a vacuum of 1.0 millimeters Hg (5–10 millimeters Hg at 100°C. is also satisfactory), until no more water distilled over. The dried ester was filtered to give 351 grams of finished ester product.

EXAMPLE 2

A 200 gram commercial sample of an isopropylphenyl diphenyl phosphate ester having a Saybolt Universal Viscosity of 150 seconds prepared in a manner similar to that of Example 1 and having an APHA color value of 400 (American Public Health Association platinum-cobalt Scale for designating color) was treated under nitrogen with 2 wt. % of tris(nonylphenyl)phosphite in 200 ml. of a 1% NaOH solution with mixing for 1 hour at 65°C and phase separated. The oil layer was then washed two times with 200 ml. of $H_2O$ at 65°C for one-half hour. The ester was dried under vacuum at 70°C/5 mm Hg. to give a finished phosphate ester having a final APHA color value of 75.

The phosphite treated ester sample was tested for PVC mill stability (which determines the effect of mill conditions on the darkening properties of a vinyl formulation incorporating the phosphate ester as a plasticizer). The phosphite treated ester passed the test. In a comparison test where the phosphate ester was washed only with dilute sodium hydroxide and then water, i.e., no phosphite ester present, the phosphate ester failed the PVC mill stability test and was darker in color (500 APHA).

Storage tests were also performed on the phosphite treated ester, which was placed in a dark closet for 10 days with no change in color.

EXAMPLE 3

200 grams of an unwashed distillate, 150 SUS, 25 APHA was treated with 2 grams of triphenylphosphite and 200 ml. of a 1% NaOH solution. The charge was mixed for 1 hour at 65°C. It was then washed twice with 100 ml. of water at 65°C. The oil phase was dried via a wiped film evaporator at 120°C/10mm. vacuum to give a finished ester having a 25 APHA. The ester did not darken upon being stored in the dark for 10 days. It passed the PVC mill stability test. Without the phosphite present the color was much darker (> 100 APHA) and the ester failed the PVC mill stability test.

What is claimed is:

1. In a method for producing alkylphenyl esters of phosphoric acid which comprises the alkylation of phenol with an olefin followed by the addition of $POCl_3$ in the presence of a Friedel-Crafts catalyst at an elevated temperature, the improvement which comprises contacting said esters with an effective amount of a phosphite ester corresponding to the formula:

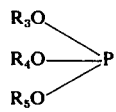

wherein $R_3$, $R_4$ and $R_5$ are radicals, each independently selected from the group consisting of alkyl, cycloalkyl, phenyl, alkylphenyl and phenylalkyl, wherein the alkyl groups contain from 1 to about 20 carbon atoms, and wherein at least one radical from the group $R_3$, $R_4$ and $R_5$ is phenyl or alkylphenyl; for a period of time sufficient to reduce the color to the desired level whereby said esters are decolorized and stabilized against subsequent color formation.

2. The method of claim 1 wherein said alkylphenyl esters correspond to the formula:

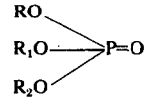

wherein R is alkaryl and $R_1$ and $R_2$ are selected from the group consisting of alkyl, aralkyl, alkaryl and aryl, and wherein the alkyl groups contain from 1 to about 20 carbon atoms.

3. The method of claim 1 wherein said alkyl groups contain from 1 to about 12 carbon atoms.

4. The method of claim 1 wherein the alkylphenyl esters contain unreacted phenols.

5. The method of claim 1 wherein said phosphite ester is a triphenyl phosphite.

6. The method of claim 1 wherein said phosphite ester is a tris(alkylphenyl) phosphite.

7. The method of claim 1 wherein said alkylphenyl ester of phosphoric acid is an isopropylphenyl phosphate.

8. The method of claim 1 wherein the alkylphenyl ester of phosphoric acid is an isopropylphenyl phenyl phosphate.

9. The method of claim 1 wherein said decolorizing and stabilizing is conducted under an inert atmosphere.

10. The method of claim 9 wherein said inert atmosphere comprises nitrogen.

11. The method of claim 1 wherein said phosphite ester is employed in an alkaline solution.

* * * * *